United States Patent [19]

Fedorov et al.

[11] Patent Number: 5,354,334
[45] Date of Patent: Oct. 11, 1994

[54] INTRAOCULAR PROSTHETIC LENS AND A METHOD FOR SURGICAL CORRECTION OF DISEASES OF THE CENTRAL SECTION OF THE RETINA

[75] Inventors: Svyatoslav N. Fedorov; Albina I. Ivashina; Andrei V. Zolotorevsky; Vladimir G. Kiselev; Anatoly N. Bessarabov; Almazbek O. Ismankulov, all of Moscow, Russian Federation

[73] Assignee: Komplex "Mikrokhirurgia Glaza" Mezhotraslevoi Nauchno-Tekhnichesky, Moscow, Russian Federation

[21] Appl. No.: 986,831

[22] Filed: Dec. 8, 1992

[30] Foreign Application Priority Data

Jun. 29, 1992 [RU] Russian Federation ............ 5049933

[51] Int. Cl.$^5$ ................................. A61F 2/16
[52] U.S. Cl. ................................. 623/6
[58] Field of Search ............... 623/6; 351/160 R, 161

[56] References Cited

U.S. PATENT DOCUMENTS

| | | | |
|---|---|---|---|
| 4,562,599 | 1/1986 | Grinder | 623/6 |
| 4,591,358 | 5/1986 | Kelman | 623/6 |
| 4,648,878 | 3/1987 | Kelmar | 623/6 |
| 4,661,109 | 4/1987 | White | 623/6 |
| 4,769,033 | 9/1988 | Nordan | 623/6 |
| 5,092,880 | 3/1992 | Ohmi | 623/6 |

Primary Examiner—Randall L. Green
Assistant Examiner—Mary Beth O. Jones
Attorney, Agent, or Firm—Keck, Mahin & Cate

[57] ABSTRACT

An optical body 1 in an intraocular prosthetic lens is made up of a first planoconvex optic element 3 and a second planoconvex optic element 4, both interconnected by their bases. An optic axis 5 of the first planoconvex optic element 3 is offset with respect to the optic axis 6 of the second planoconvex optic element 4.

5 Claims, 3 Drawing Sheets

INTRAOCULAR PROSTHETIC LENS AND A METHOD FOR SURGICAL CORRECTION OF DISEASES OF THE CENTRAL SECTION OF THE RETINA

TECHNICAL FIELD

This invention relates generally to medicine and more specifically to ophthalmology; it can be applied for correction of visual functions in patients with affected central section of the retina.

Correction of visual defects such as myopia, hyperopia, and some other has so far made use of spectacles or contact lenses. However, visual correction with the aid of such devices is a provisional measure, since they are to be removed and mounted periodically, e.g., during skiing, swimming, and so on.

BACKGROUND OF THE INVENTION

To solve these problems resort has been made to intraocular lenses or artificial lenticulus though they have been used largely for correction of aphakia following cataract extraction.

The present state of ophthalmological practice knows many intraocular prosthetic lenses, comprising an optic body and supporting elements. The optical portion of all such intraocular lenses is in effect a positive (convex) lens. Light rays refracted by the optical part of such intraocular lenses are focused in the macular region. Among such intraocular lenses is the one according to U.S. Pat. No. 4,661,109 with a priority of Apr. 28, 1987, which comprises an optic body shaped as a planoconvex element and S-like open supporting members. However, this intraocular lens is for surgical correction of cataract and therefore cannot be used for treatment of affections of the central retinal section of the eye.

At present there are a great number of patients suffering from affections of the central retinal section, especially among those of the elderly and old age, wherein affection with maculardystrophy occurs in 25–40 percent of all ophthalmopathological cases. It is very frequently that the fellow eye gets involved so that in 5–8 years since the onset of the disease about 70 percent of patients suffer from central blindness in botheyes, the visual acuity being 0.1 or below. Implantation of conventional intraocular lenses fails to improve the visual function in such patients, since the image gets on the affected retinal area. Thus the problem of restoration of visual functions arises in patients with diseases of the central retinal section.

One more state-of-the-art intraocular lens (U.S. Pat. No. 4,562,599 with a priority of Jan. 7, 1986) known to comprise an optic body shaped as a planoconvex element and S-like closed supporting members.

However, implantation of such an intraocular lens into the eye of a patient suffering from affection of the central retinal section fails to solve the problem of visual correction, since with the use of the present introcular lens the retinal image is formed in the macular region, which is affected in such patients.

Another state-of-the-art intraocular lens (U.S. Pat. No. 4,591,358 with a priority of May 27, 1986) is known to comprise an optic body shaped as a planoconvex element and four symmetric arcuate supporting members facing with their convex surface towards the optic body.

However, application of this intraocular lens fails to provide correction of visual functions in patients with the affected central retinal section, since the optic axis of said lens aligns with the central optic axis of the eye so that light rays refracted in the optic body of the lens are focused in the macular region. Inasmuch as said region is affected, the central retinal section cannot perceive the image and implantation of such an intraocular lens fails to provide correction of visual functions.

SUMMARY OF THE INVENTION

It is a primary and essential object of the invention to provide such an intraocular prosthetic lens that would allow one to displace the retinal image onto the paramacular retinal region from the affected region in patients with affected central macular section and thus to correct visual functions in such a contingent of patients.

This object is accomplished due to the fact that in an intraocular lens comprising an optic body and supporting members, the optical body is made up of a first planoconvex element and a second planoconvex element, which are interconnected by flat surfaces, and the optic axis of the first planoconvex optic element is offset with respect to the optic axis of the second planoconvex element.

Provision of the optical part of the intraocular lens in question made up of two planoconvex optic elements interconnected by flat surfaces with the optic axis of the first planoconvex element offset relative to the optic axis of the second planoconvex element makes it possible to displace the retinal image onto the paramacular retinal region.

There has been developed one more variant of an intraocular lens, comprising an optic body made up of a first plano-convex optic element and a second planoconvex optic element interconnected by flat surfaces, and the optic axis of the first planoconvex optic element is offset with respect to the optic element of the second planoconvex optic element, while the radius of curvature of the first optic element is equal to that of the second optic element interconnected with the first one.

There is provided an alternative embodiment of an intraocular lens, comprising an optic body and supporting elements, wherein the optic body is made up of a first planoconvex element and a second planoconvex element interconnected by flat surfaces, the optic axis of the first planoconvex element being offset relative to the optic axis of the second planoconvex element, while the radii of curvature of the interconnected optic elements differ from each other.

The values of the radii of curvature of the first and second planoconvex optic elements depend on the anatomical and optical parameters of the patient's eye. The amount of displacement of the optic axis of the second planoconvex optic element with respect to the optic axis of the first planoconvex optic element depends also on the parameters of the patient's eye and the place of the affection focus on the reticular surface, said amount being calculated individually for every particular patient, using an empirical formula derived by the inventors and cannot go beyond the limits of a certain numerical range for the construction of the proposed intraocular lens.

A further alternative embodiment of the intraocular lens provides for an optic body and supporting members, said optic body being made up of a first planoconvex optic element and a second planoconvex optic element, both being interconnected by flat surfaces. The optic axis of the first planoconvex optic element is offset with respect to the optic axis of the second planoconvex optic element, while a mark is provided on the peripheral portion of the first optic element at the place of maximum displacement of the first optic element relative to the second optic element.

Provision of a mark on the peripheral portion of the first lens at the place of maximum displacement of the first optic element with respect to the second optic element provide for accurate setting of the proposed intraocular lens in the posterior eye chamber so as to displace the retinal image for a certain preset value.

A method is described for surgical correction of vision with the aid of the proposed intraocular lens in patients with affected central retinal section.

A method for surgical correction of vision in diseases of the central retinal section with the aid of the intraocular lens is characterized in that:

(a) the condition of the central retinal section is assessed.

(b) for detection of affection of the central retinal section, there is carried out central static perimetry for an angular value up to 30° from the retinal macula lutes for assessing its functional state, whereupon the affection focus is localized;

(c) the point of new image fixation is selected, spaced 18 degrees apart from the macula lutea, provided that relatively intact local areas of the retina are present, (d) the amount of displacement of the optic axis of the first planoconvex optic element with respect to the optic axis of the second planoconvex optic element is so selected that the total angle of displacement be equal to a value required for formation of the new point of fixation on the preselected local area;

(e) the crystalline lens of the eye is removed, the posterior lenticular capsule remaining unaffected, and an intraocular prosthetic lens is implanted, comprising an optic body and supporting elements, wherein the optic body is made up of a first planoconvex optic element and a second plano-convex optic element, both of them being interconnected by flat surfaces, the axis of the first planoconvex optic element being offset with respect to the optic axis of the second planoconvex optic element, while a mark is provided on the peripheral portion of the first optic element at the place of maximum displacement of the first optic element relative to the second one, the first optic element being so oriented that the mark should face the direction of the preselected displacement of the image.

BRIEF DESCRIPTION OF THE DRAWINGS

In what follows the invention is exemplified by the disclosure of specific embodiments of an intraocular lens to be read in conjunction with the accompanying drawings, wherein.

DETAILED DESCRIPTION OF THE INVENTION

Figure 1:
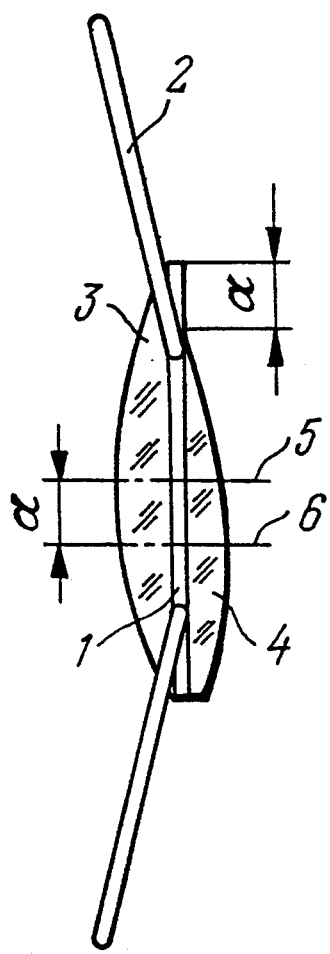
FIG. 1 is a side view of an intraocular prosthetic lens.
Figure 2:
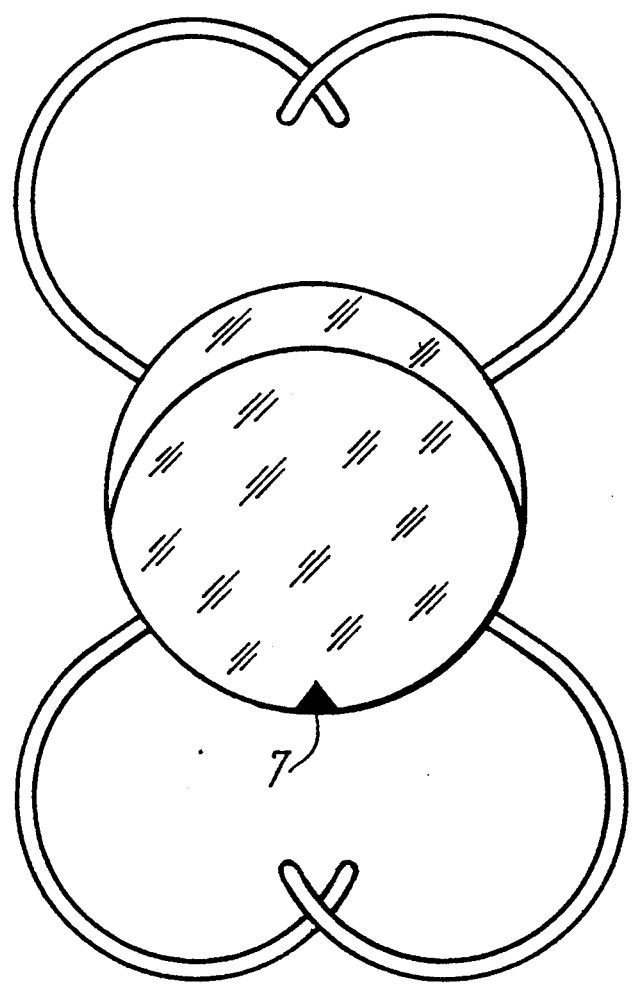
FIG. 2 is a front view of an intraocular prosthetic lens.

The intraocular prosthetic lens (FIGS. 1, 2) comprises an optic body 1 and supporting elements 2. The optic body 1 is made up of two planoconvex optic elements. A first plano-convex optic element 3 and a second planoconvex optic element 4 are interconnected by plane surfaces. The position of the first planoconvex optic element 3 with respect to the second planoconvex optic element 4 is such that an optic axis 5 of the first planoconvex optic element 3 is offset relative to an optic axis 6 of the second planoconvex element 4. The amount "$\alpha$" of displacement of the axes 5 and 6 is calculated using an empirically derived mathematical relationship for every particular patient. The radius of curvature of the first planoconvex optic element 3 may be equal to the radius of curvature of the second planoconvex optic element 4.

According to an alternative embodiment of the present invention the length of the radius $R_1$ of curvature of the first panoconvex optic element 3 may differ from the length of the radius $R_2$ of the second planoconvex optic element 4. Such an embodiment of the lenses depends on the anatomical and optic parameters of the patient's eye.

Figure 3:
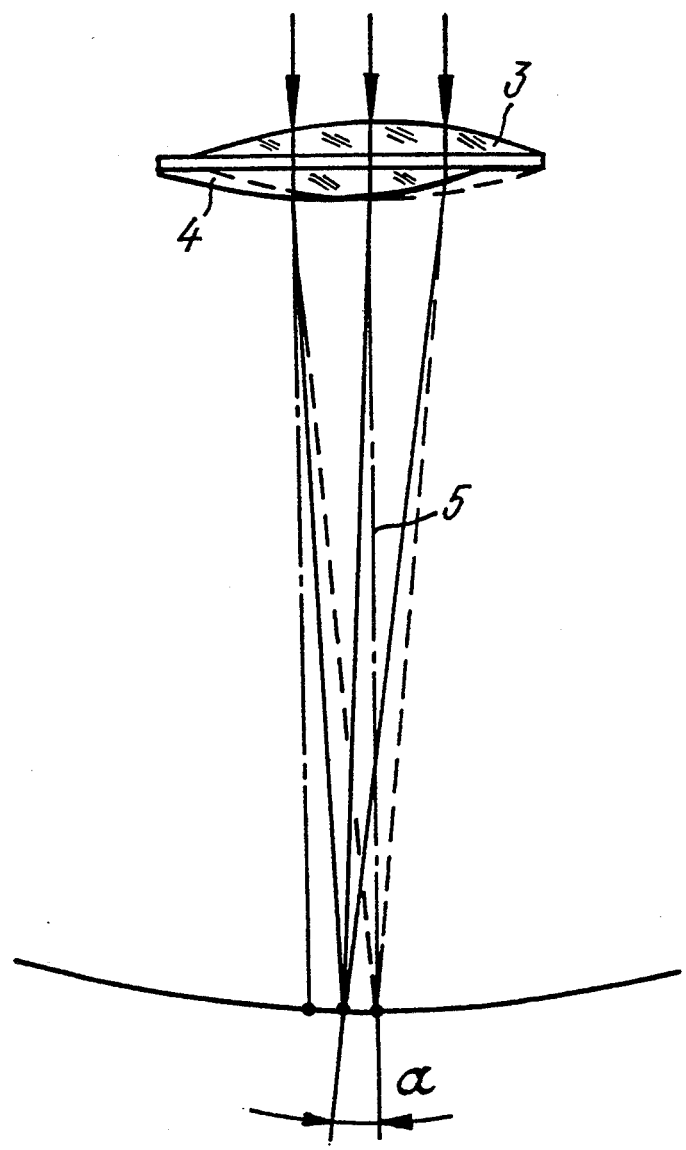
FIG. 3 is a diagram of light path through the intraocular lens.
Figure 4:
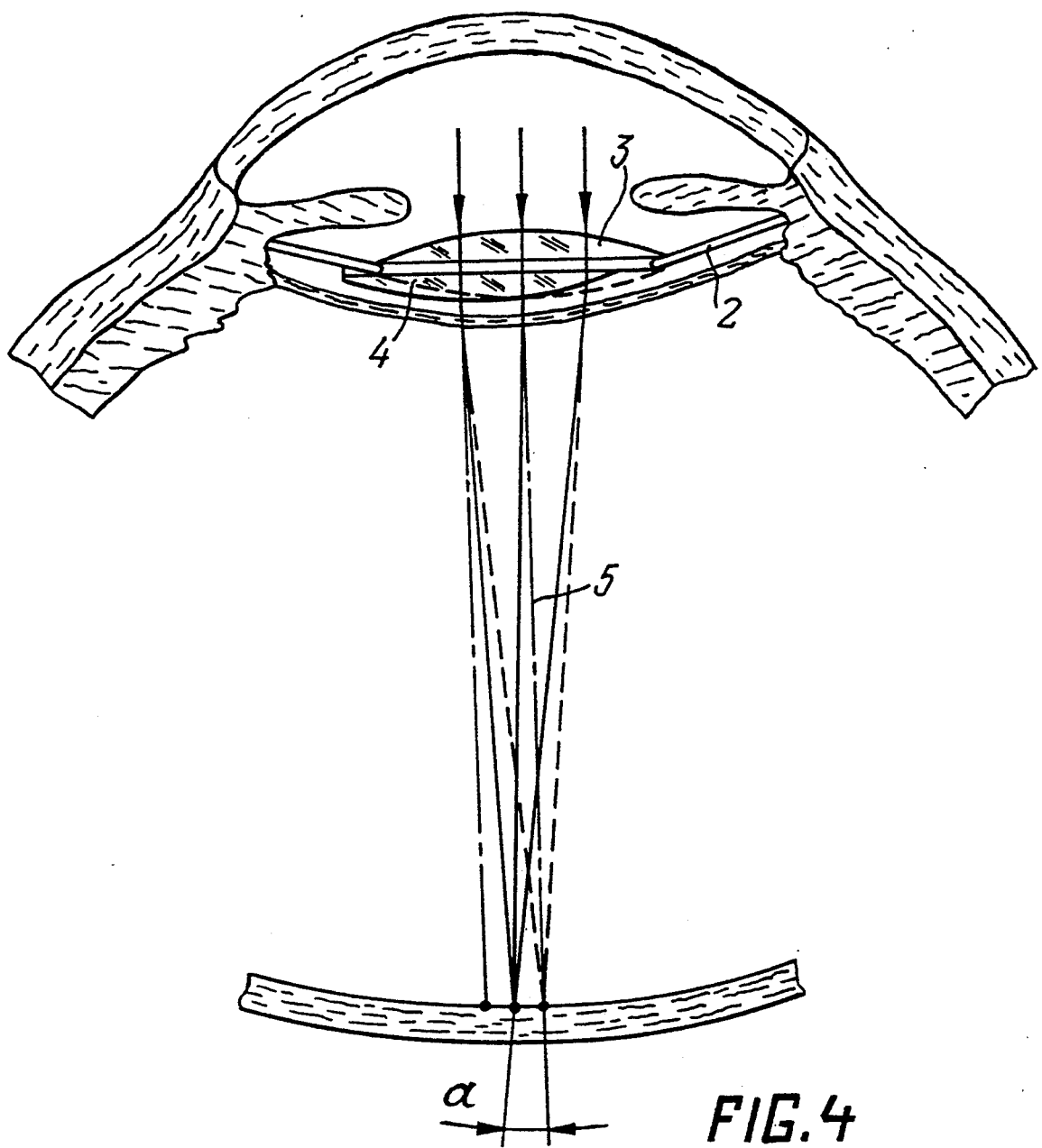
FIG. 4 shows the position of the intraocular lens when implanted in the eye.

A mark 7 is provided on the peripheral portion of the first planoconvex optic element 3 at the place of maximum displacement of the first optic element 3 with respect to the second optic element 4, said mark being aimed at plane orientation of the intraocular lens in the patient's eye. The path of light rays (FIG. 3) through the optic body 1 of the intraocular length establishes an angle of deflection of optic rays with respect to the optic axis 5 of the first planoconvex optic element 3. The supporting elements 2 of the proposed intraocular prosthetic lens are so made as to provide implantation of said prosthetic lens into the posterior eye chamber (FIG. 4). The shape of the supporting elements 2 may be, e.g., according to U.S. Pat. No. 4,838,890 of June, 1989.

Surgical correction of vision in diseases of the central retinal section is effected as follows:

In the preoperative period all the patients are subjected to examinations aimed at impartial assessment of the state of the central retinal section using opthalmoscopy, followed by central static perimetry for an angular value up to 30° from the macula lutea for detecting the affection of the central retinal section for assessing its functional state. When evaluating the results of computer-aided perimetry special attention should be paid to the absolute values of photosensitivity rather than to relative values, since any reduction of absolute photosensitivity values may be due to opacity of the crystalline lens. Correlation between the findings of functional examinations and those of clinical study is also of importance. Upon evaluating the data of static computer-aided perimetry there is carried out visual inspection of the ocular fundus so as to select the new fixation point for an angular value of 18 degrees from the macula lutea, provided relatively intact local areas of the retina are present.

Intraocular lens is selected in accordance with the anatomical parameters of the patient's eye. The amount of displacement of the optic axis 5 of the first planoconvex optic element 3 with respect to the optic axis 6 of the second planoconvex optic element 4 is calculated so that the total angle of deflection of light rays is equal to a value required for formation of the new fixation point in the preselected local retinal area. The amount of displacement of the optic axes of the two optic elements is calculated using an empirically derived mathematical formula individually for every particular patient.

The crystalline lens of the patient's eye is removed so as to retain the posterior lenticular capsule intact, whereupon an intraocular prosthetic lens is implanted, comprising an optic body and supporting elements, wherein the optic body is made up of the first and second planoconvex optic elements 3 and 4, respectively, interconnected by plane surfaces, the optic axis 5 of the first planoconvex optic element 3 being offset with respect to the optic axis 6 of the second planoconvex optic element 4, while the mark 7 is provided on the peripheral portion of the first optic element 3 at the place of maximum displacement of the first optic element 3 with respect to the second optic element 4.

The proposed intraocular prosthetic lens is implanted as follows:

The intraocular lens is implanted into the posterior eye chamber, the implantation technique depending upon the construction of the supporting elements 2. A specific feature of implantation of the proposed intraocular lens resides in the fact that its plane orientation is performed depending upon the anatomy of the pathological focus.

When implanting the intraocular lens into the posterior eye chamber the lens is so turned that the mark 7 provided on the peripheral portion of the first optic element 3 should face the preselected direction of image displacement in the preselected local retinal area.

Clinical case reports.

EXAMPLE 1

Male patient Sh., 69. Diagnosis: immatura cataract in OD, central atherosclerotic chorioretinopathy in both eyes. Preoperative visual acuity: OD 0.04, OS 0.2. Both eyes were not correctable.

Static computer-aided perimetry revealed relative scotoma, 1000 asb deep, having an angular size up to 15 degrees off the fixation point. The scotoma was extended along the vertical axis up to 15 degrees and along the horizontal axis up to 7 degrees.

Furthermore, the disciform stage of senile macular dystrophy was diagnosed clinically.

The patient was subjected to implantation of an intraocular lens, according to the present invention, using the hereindisclosed method.

The intraocular lens was implanted in the capsular bag in such a manner that the mark should face towards the patient's nose, taking account of individual features of the functional state of the retina.

Both the surgery and postoperative period were uneventful.

Status after surgery: visual acuity OD−0.1. The anterior eye chamber of medium depth, the implanted intraocular lens in correct position.

As a result of surgery performed there was formed the new image fixation point in the unaffected reticular zone.

EXAMPLE 2

Female patient Ch., 77. Diagnosis: primary cataract in the left eye, central senile macular degeneration in both eyes. Preoperative visual acuity: OD 0.1, OS 0.04, Both eyes were not correctable.

Static computer-aided perimetry revealed relative scotoma, 1000 asb deep, measuring up to 10 degrees off the fixation point. The scotoma was extended up to 10 degrees along the vertical axis and up to 5 degrees along the horizontal axis. The disciform stage of senile macular dystrophy was diagnosed clinically.

The patient was subjected to implantation of an intraocular lens, according to the present invention, using the herein-disclosed method.

The intraocular lens was implanted into the capsular bag in such a manner that the mark should face towards the patient's temple, taking account of individual features of the functional state of the retina.

Both the surgical procedure and the postoperative period were uneventful.

Status on Feb. 20, 1991. Visual acuity OS−0.15; the anterrior eye chamber of medium depth. The implanted intraocular lens in correct position.

As a result of surgery performed there was formed the new image fixation point in the unaffected reticular zone.

Thus implantation of the proposed intraocular prosthetic lens makes it possible to correct visual functions in patients with affected central reticular section and to enhance visual functions from 0.01 to 0.15.

What is claimed is:

1. An intraocular prosthetic lens, comprising an optic body and supporting members, wherein the optic body is made up of a first planoconvex optic element and a second planoconvex optic element, both being interconnected by plane surfaces, and the optic axes of both elements are substantially parallel to the optic axis of the eye and offset relative to each other in a direction perpendicular to the optic axis of the eye.

2. An intraocular prosthetic lens according to claim 1, wherein a radius of curvature of the first optic element is equal to that of the second optic element.

3. An intraocular prosthetic lens according to claim 1, wherein radii of curvature of the interconnected optic elements differ from each other.

4. An intraocular prosthetic lens according to claim 1, wherein a mark is provided on a peripheral portion of the first optic element at a place of maximum displacement of the first optic element with respect to the second optic element.

5. A method for surgical correction of vision in diseases of the central retinal section of a human eye, with the aid of an intraocular prosthetic lens according to claim 1, comprising:
 (a) assessing the condition of the eye;
 (b) detecting an affection of the central retinal section, and performing central static perimetry for an angular value up to 30° from the macula lutea to evaluate its functional state;
 (c) selecting a new image fixation point, spaced 18 degrees from the macula lutea, in an area of the retina having relatively unaffected local areas;
 (d) selecting an amount of displacement of an optic axis of the first planoconvex optic element with respect to the optic axis of the second planoconvex optic element wherein total angle of displacement is equal to a value required for formation of a new image fixation point on a preselected local area;
 (e) removing the crystalline lens of the eye, the posterior capsule remaining unaffected, and implanting the intraocular prosthetic lens wherein a mark is provided on a peripheral portion of the first optic element at the place of maximum displacement of the first optic element relative to the second optic element, the first optic element being oriented so that the mark faces the direction of the image.

* * * * *